United States Patent [19]

Chiang et al.

[11] Patent Number: 5,053,227
[45] Date of Patent: Oct. 1, 1991

[54] SKIN PERMEATION ENHANCER COMPOSITIONS, AND METHODS AND TRANSDERMAL SYSTEMS ASSOCIATED THEREWITH

[75] Inventors: Chia-Ming Chiang, Foster City; Gary W. Cleary, San Mateo, both of Calif.

[73] Assignee: Cygnus Therapeutic Systems, Redwood City, Calif.

[21] Appl. No.: 537,080

[22] Filed: Jun. 12, 1990

Related U.S. Application Data

[62] Division of Ser. No. 327,312, Mar. 22, 1989, Pat. No. 4,973,468.

[51] Int. Cl.$^5$ ............................................. A61F 13/02
[52] U.S. Cl. .................................... 424/448; 424/449; 424/447; 514/946; 514/947
[58] Field of Search ................ 424/449, 448; 514/946, 514/947

[56] References Cited

U.S. PATENT DOCUMENTS

| | | | |
|---|---|---|---|
| 3,472,931 | 10/1969 | Stoughton | 514/50 |
| 3,551,554 | 12/1970 | Herschler | 424/7.1 |
| 3,598,122 | 8/1971 | Zaffaroni | 424/435 |
| 3,598,123 | 8/1971 | Zaffaroni | 424/434 |
| 3,731,683 | 5/1973 | Zaffaroni | 424/434 |
| 3,742,951 | 7/1973 | Zaffaroni | 424/434 |
| 3,797,494 | 3/1974 | Zaffaroni | 424/434 |
| 3,854,480 | 12/1974 | Zaffaroni | 424/424 |
| 3,923,989 | 12/1975 | Anderson | 514/344 |
| 3,926,188 | 12/1975 | Baker et al. | 424/427 |
| 3,964,482 | 6/1976 | Gerstel et al. | 424/449 |
| 3,989,816 | 11/1976 | Rajadhyaksha | 424/68 |
| 4,006,218 | 2/1977 | Sipos | 514/29 |
| 4,316,893 | 2/1982 | Rajadhyaksha | 514/24 |
| 4,379,454 | 4/1983 | Campbell | 424/448 |
| 4,405,616 | 9/1983 | Rajadhyaksha | 514/788 |
| 4,435,180 | 3/1984 | Leeper | 424/440 |
| 4,440,771 | 4/1984 | Zupan | 514/420 |
| 4,460,372 | 7/1984 | Campbell et al. | 424/449 |
| 4,537,776 | 8/1985 | Cooper | 514/549 |
| 4,552,872 | 11/1985 | Cooper et al. | 514/174 |
| 4,557,934 | 12/1985 | Cooper et al. | 424/449 |
| 4,559,222 | 12/1985 | Enscore et al. | 424/486 |
| 4,568,343 | 2/1986 | Leeper et al. | 424/449 |
| 4,704,282 | 11/1987 | Campbell et al. | 424/449 |
| 4,717,568 | 1/1988 | Eckenhoff et al. | 424/449 |
| 4,746,509 | 5/1988 | Haggiage et al. | 424/449 |
| 4,746,515 | 5/1988 | Cheng et al. | 424/449 |
| 4,764,379 | 8/1988 | Sanders et al. | 424/449 |
| 4,783,450 | 11/1988 | Fawzi et al. | 514/78 |
| 4,788,062 | 11/1988 | Gale et al. | 424/449 |

FOREIGN PATENT DOCUMENTS

| | | |
|---|---|---|
| 0235090 | 9/1987 | European Pat. Off. |
| 0261429 | 3/1988 | European Pat. Off. |
| 87402945.7 | 6/1988 | European Pat. Off. |
| 0275716 | 7/1988 | European Pat. Off. |
| 0279982 | 8/1988 | European Pat. Off. |
| 0285563 | 10/1988 | European Pat. Off. |
| 88/01496 | 3/1988 | PCT Int'l Appl. |

*Primary Examiner*—Thurman K. Page
*Assistant Examiner*—Leon R. Horne
*Attorney, Agent, or Firm*—Dianne E. Reed

[57] ABSTRACT

Skin permeation enhancer compositions are provided which increase the permeability of skin to transdermally administered pharmacologically active agents. The composition contains diethylene glycol monoethyl or monomethyl ether in addition to an ester component such as propylene glycol monolaurate, methyl laurate or the like. The compositions are particularly useful in conjunction with the transdermal administration of steroid drugs such as progestogens and estrogens. Methods and drug delivery systems for using the enhancer compositions are provided as well.

9 Claims, 1 Drawing Sheet

SKIN PERMEATION ENHANCER COMPOSITIONS, AND METHODS AND TRANSDERMAL SYSTEMS ASSOCIATED THEREWITH

This application is a division of application Ser. No. 07/327,312 filed, Mar. 22, 1989, now U.S. Pat. No. 4,973,468.

DESCRIPTION

1. Technical Field

This invention relates generally to the transdermal administration of pharmacologically active agents and more particularly relates to methods and compositions for enhancing the permeability of the skin to such agents.

2. Background

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10-15 microns thick over most of the body. It is believed to be the high degree of keratinization within these cells as well as their dense packing which creates in most cases a substantially impermeable barrier to drug penetration.

In order to increase skin permeability, and in particular to increase the permeability of the stratum corneum (i.e., so as to achieve enhanced penetration, through the skin, of the drug to be administered transdermally), the skin may be pretreated with a penetration enhancing agent (or "permeation enhancer", as sometimes referred to herein) prior to application of a drug. Alternatively, and preferably, a drug and a permeation enhancer are concurrently delivered.

The present invention is directed to a novel composition for enhancing the penetration of pharmacologically active agents through skin, the composition in a preferred embodiment comprising a combination of diethylene glycol monoethyl ether (available under the trademark Transcutol from Gattefosse; sometimes referred to herein as "TC") with at least one long-chain ester, e.g., of lauric acid, including glycerol monolaurate ("GML"), propylene glycol monolaurate ("PGML"), propylene glycol dilaurate ("PGDL") methyl laurate ("ML") ethyl laurate ("EL") or the like. Surprisingly, this combination has been found by the inventor herein to be more effective in enhancing the penetration of pharmacologically active agents through skin than either Transcutol or a lauric acid ester alone. The novel enhancer composition is particularly effective in conjunction with the transdermal administration of steroid drugs.

While there are a number of patents and publications available which relate to the transdermal administration of steroid drugs, to the use of Transcutol as a skin permeation enhancer, and to combination-type enhancer compositions, applicant is unaware of any art which relates to the "combination" enhancer composition disclosed and claimed herein or to the use of such an enhancer composition with a steroid drug.

DESCRIPTION OF THE PRIOR ART

Skin permeation enhancers: Various compounds for enhancing the permeability of skin are known in the art. U.S. Pat. Nos. 4,006,218, 3,551,554 and 3,472,931, for example, respectively describe the use of dimethylsulfoxide (DMSO), dimethyl formamide (DMF) and N,N-dimethylacetamide (DMA) to enhance the absorption of pharmacologically active agents through the stratum corneum. Other compounds which have been used to enhance skin permeability include: decylmethylsulfoxide ($C_{10}MSO$); Transcutol, cited in the preceding section; polyethylene glycol monolaurate (PEGML; see, e.g., U.S. Pat. No. 4,568,343); glycerol monolaurate (U.S. Pat. No. 4,746,515); propylene glycol monolaurate (see European Patent Application No. 87402945.7, published as EP Publication No. 272 987, which derives from U.S. Pat. application Ser. No. 945,356, filed Dec. 22, 1986, of common assignment herewith): ethanol (e.g., as in U.S. Pat. No. 4,379,454); eucalyptol (U.S. Pat. No. 4,440,777); lecithin (U.S. Pat. No. 4,783,450); the 1-substituted azacycloheptan-2-ones, particularly 1-n-dodecylcylclazacylcoheptan-2-one (available under the trademark Azone ® from Nelson Research & Development Co., Irvine, CA; see U.S. Pat. Nos. 3,989,816, 4,316,893, 4,405,616 and 4,557,934); propylene glycol in combination with a fatty acid such as linoleic acid (European patent publication No. 261429): "cell envelope disordering compounds" such as methyl laurate or oleic acid in combination with N-(hydroxyethyl) pyrrolidone (U.S. Pat. No. 4,537,776) or $C_3$-$C_4$ diols (U.S. Pat. No. 4,552,872, European Patent Application Publication No. 043738). U.S. Pat. No. 4,764,379 discloses a binary enhancer composition of ethanol and glycerol monolaurate.

Transdermal administration of steroid drugs: U.S. Pat. Nos. 4,379,454, 4,460,372, 4,559,222, 4,568,343 (cited above with respect to the use of PEGML as a permeation enhancer) and European Patent Publication No. 285563 relate to the transdermal administration of estrogens, while U.S. Pat. No. 4,435,180 provides an example (Example IV at col. 7) which describes a system for the transdermal administration of progesterone. Concurrent administration of progesterone and estradiol esters is described in U.S. Pat. No. 4,788,062. PCT Publication WO88/01496 and European Patent Publication No. 275716 both describe transdermal administration of a composition containing both an estrogen and a progestogen. In addition, European patent Publication No. 235090 relates to the transdermal administration of an ethinyl estradiol/norethindrone acetate composition, while European Patent Publication No. 279982 describes a transdermal delivery system for the concurrent administration of ethinyl estradiol and levonorgestrel. U.S. Pat. No. 4,746,515, cited above as describing the use of GML as a permeation enhancer, also relates to the transdermal administration of steroid drugs. U.S. Pat. No. 4,704,282 relates to a transdermal drug delivery system for the administration of progesterone, testosterone and hydrocortisone. Other patents which relate to transdermal drug delivery devices stated to be useful in the administration of steroid drugs include U.S. Pat. Nos.: 3,598,122; 3,598,123; 3,731,683; 3,797,494; 3,854,480; 3,923,939; 3,926,188; 3,964,482; and 4,717,568.

DISCLOSURE OF THE INVENTION

Accordingly, it is an object of the present invention to provide a skin permeation enhancer composition comprising a first component that is an ether selected from the group consisting of diethylene glycol monoethyl ether and diethylene glycol monomethyl ether and a second component that is an ester given by the formula $[CH_3(CH_2)_mCOO]_nR$, in which m is an integer from 8 to 16, preferably 8 to 12, most preferably 10, n is 1 or 2, preferably 1, and R is a lower alkyl ($C_1$–$C_3$) residue which may or may not be substituted with 1 or 2 hydroxyl groups.

It is another object of the present invention to provide a composition of matter useful for the delivery of a pharmacologically active agent through skin, comprising the above-described enhancer composition in combination with a selected pharmacologically active agent.

It is still another object of the invention to provide such a composition in which the pharmacologically active agent is a steroid drug.

It is a further object of the invention to provide methods and transdermal delivery systems for using the aforementioned compositions.

Additional objects, advantages and novel features of the invention will be set forth in part in the description which follows, and in part will become apparent to those skilled in the art upon examination of the following, or may be learned by practice of the invention.

In one aspect of the invention, a composition of matter is provided that is useful for the delivery of a pharmacologically active agent through the skin, comprising:

(a) a therapeutically effective amount of the at least one pharmacologically active agent: and (b) an amount of a permeation enhancer composition effective to enhance the penetration of the at least one pharmacologically active agent through skin, the enhancer composition comprising an ether component selected from the group consisting of diethylene glycol monoethyl ether and diethylene glycol monomethyl ether, and an ester component given by the formula $[CH_3(CH_2)_mCOO]_nR$, in which m is an integer from 8 to 16, n is 1 or 2, and R is a lower alkyl ($C_1$–$C_3$) residue which is either unsubstituted or substituted with one or two hydroxyl groups.

In another aspect of the invention, a method is provided that is useful for enhancing the skin penetration of a pharmacologically active agent, comprising applying to the skin, in addition to a therapeutically effective amount of the pharmacologically active agent, a permeation enhancer composition comprising an ether component selected from the group consisting of diethylene glycol monoethyl ether and diethylene glycol monomethyl ether, and an ester component given by the formula $[CH_3(CH_2)_mCOO]_nR$, in which m, n and R are as defined above.

In still another aspect of the invention, a system is provided useful for the transdermal administration of a pharmacologically active agent, comprising:

(a) a source of the pharmacologically active agent;

(b) a source of a permeation enhancer composition comprising an ether component selected from the group consisting of diethylene glycol monoethyl ether and diethylene glycol monomethyl ether, and an ester component given by the formula $[CH_3(CH_2)_mCOO]_nR$ with m, n and R as defined above; and (c) a means for maintaining the system in agent and enhancer composition transmitting relationship to the skin.

MODES FOR CARRYING OUT THE INVENTION

Figure 1:
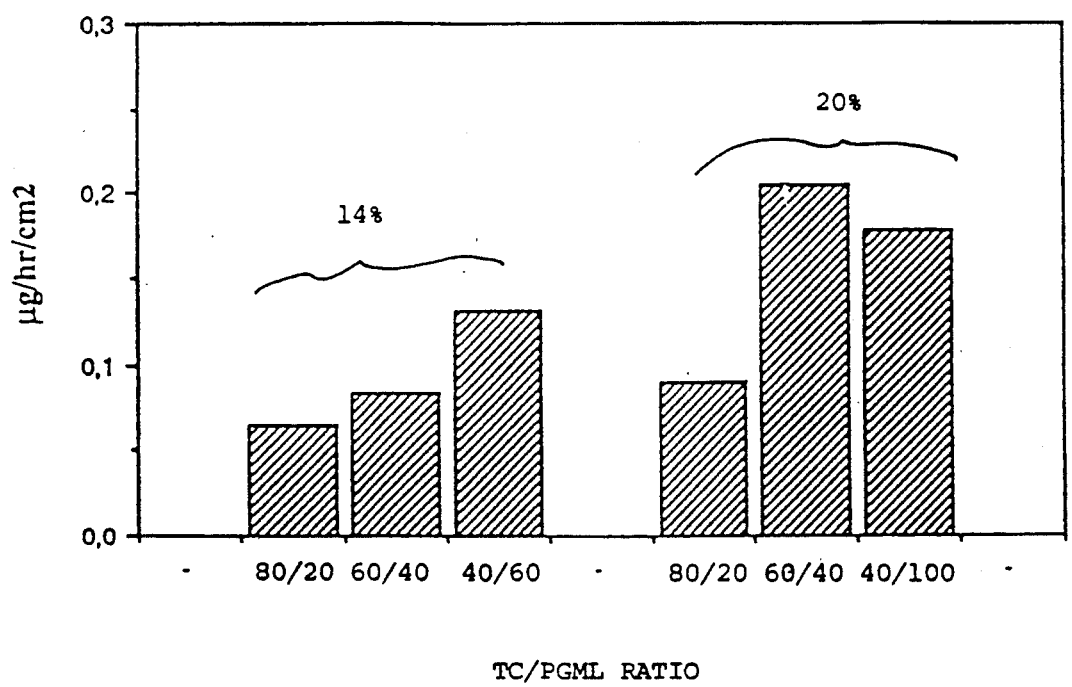
FIG. 1 is a graphic representation of the composition optimization results obtained in Example 6.

"Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers, and, in particular, through the use of the enhancer composition of the present invention, can be observed by measuring the rate of diffusion of drug through animal or human skin using a diffusion cell apparatus as described in the Examples herein.

By "transdermal" delivery, applicants intend to include both transdermal (or "percutaneous") and transmucosal administration, i.e., delivery by passage of a drug through the skin or mucosal tissue and into the bloodstream.

"Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition in a deleterious manner. Examples of suitable carriers for use herein include water, mineral oil, silicone, liquid sugars, waxes, petroleum jelly, and a variety of other oils and polymeric materials. In addition, one or both of the components of the present enhancer composition may also serve as a carrier.

By the term "pharmacologically active agent" or "drug" as used herein is meant any chemical material or compound suitable for transdermal or transmucosal administration which induces a desired systemic effect. Such substances include the broad classes of compounds normally delivered through body surfaces and membranes, including skin. In general, this includes: antiinfectives such as antibiotics and antiviral agents; analgesics and analgesic combinations; anorexics; antihelminthics: antiarthritics; antiasthmatic agents: anticonvulsants; antidepressants; antidiabetic agents; antidiarrheals; antihistamines; antiinflammatory agents; antimigraine preparations: antinauseants: antineoplastics: antiparkinsonism drugs: antipruritics: antipsychotics: antipyretics: antispasmodics: anticholinergics; sympathomimetics; xanthine derivatives: cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants: hormones such as estradiol and other steroids, including corticosteroids; hypnotics; immunosuppressives; muscle relaxants; parasympatholytics; psychostimulants; sedatives; and tranquilizers.

Steroid drugs represent a preferred class of drugs for use in conjunction with the enhancer composition of the present invention. Examples of steroid drugs useful herein include: progestogens such as norethindrone, norethindrone acetate, desogestrel, 3-keto desogestrel, gestadene and levonorgestrel; estrogens such as estradiol and its esters, e.g., estradiol valerate, cyprionate, decanoate and acetate, as well as ethinyl estradiol; corticosteroids such as cortisone, hydrocortisone, fluocinolone acetonide; and testosterone. In a particularly preferred embodiment, the compositions of the invention include one or more estrogens as well as one or more progestogens.

By "therapeutically effective" amount of a pharmacologically active agent is meant a nontoxic but sufficient amount of a compound to provide the desired therapeutic effect. An "effective" amount of a permeation enhancer as used herein means an amount that will provide the desired increase in skin permeability and, correspondingly, the desired depth of penetration, rate of administration, and amount of drug delivered.

In a preferred embodiment, the enhancer composition of the invention contains a first, ether, component which is diethylene glycol monoethyl or monomethyl ether, and a second, ester, component given by the formula $[CH_3(CH_2)_mCOO]_nR$ with m, n and R as defined above, wherein the preferred ratio (v/v) of the ether to the ester components in the enhancer composition ranges from about 90:10 to about 10:90, more preferably from about 90:10 to about 40:60. This ratio represents the relative amounts of the ether and ester components in the initial formulation of the enhancer composition. The preferred ratio may vary depending on whether the enhancer composition is applied directly to the skin in an ointment, gel or the like, or whether it is incorporated into one or more layers of a transdermal drug delivery device. The preferred ratio may also vary with the specific components selected for the enhancer composition.

The ester component represented by the formula $[CH_3(CH_2)_mCOO]_nR$ with m, n and R as above, contains 1 or 2, preferably 1, 10- to 18-carbon chains (i.e., wherein m is 8 to 16) bound to a central lower alkyl ($C_1$–$C_3$) moiety which may be either unsubstituted or substituted with one or two hydroxyl groups. Thus, the component may include one or two capric, lauric, myristic, palmitic or stearic acid residues. In the preferred embodiment herein, the ester component is a lower alkyl ($C_1$–$C_3$) laurate (i.e., m is 10 and n is 1), and in a particularly preferred case is "PGML". It will be appreciated by those skilled in the art that the commercially available material sold as "PGML" is typically a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. The present invention accordingly encompasses both the mixture of compounds which will typically be present in commercially available PGML, and as well as pure propylene glycol monolaurate itself.

In addition to the ester component, as noted above, the enhancer composition also contains diethylene glycol monoethyl or monomethyl ether, or both, preferably the monoethyl ether, i.e., Transcutol. While the ether and ester components have been sometimes referred to herein as the "first" and "second" components, it will be appreciated by those skilled in the art that the composition may contain both the monoethyl and monomethyl ether, and may in addition include more than one ester component.

As will be established in the examples which follow, the combination of the ether and ester components increases the skin flux of a selected drug, generally, relative to the use of either type of component alone (It should be noted, however, that the flux of a given drug through skin will vary with the drug or drugs selected for administration, the structure of the transdermal delivery device used, if any, and the vehicles incorporated into the drug-containing composition.) With certain drugs, one or both of the components may in addition act as a solubilizer or vehicle.

The composition may in addition include one or more selected carriers or excipients, and various agents and ingredients commonly employed in dermatological ointments and lotions. For examples, fragrances, opacifiers, preservatives, anti-oxidants, gelling agents, perfumes, thickening agents, stabilizers, surfactants, emollients, coloring agents, and the like may be present.

The relative amounts of the components in these compositions can vary a great deal. For example, the amount of drug or drugs present in the composition will depend on a variety of factors, including the disease to be treated, the nature and activity of the drug, the desired effect, possible adverse reactions, the ability and speed of the drug to reach its intended target, and other factors within the particular knowledge of the patient and physician. The amount of enhancer present in the composition will similarly depend on a number of factors, e.g., on the depth of cutaneous penetration desired, the strength of the particular enhancer, on the specific drug or drugs selected, and the like.

The method of delivery of the present compositions may also vary, but necessarily involves applying the selected composition to a defined surface of the skin or other tissue for a period of time sufficient to provide the desired blood level of drug for the desired period of time. The method may involve direct application of the composition as an ointment, gel, cream, or the like, or may involve use of a drug delivery device as taught, for example, in U.S. Pat. Nos. 3,742,951, 3,797,494 or 4,568,343, and in commonly assigned U.S. patent Application Serial No. 945,356, cited supra.

A transdermal delivery system can be constructed with the enhancer composition described hereinabove to deliver drugs for sustained drug delivery. The targeted skin flux for delivery of a particular drug can be achieved by adjusting vehicle composition and vehicle loading, as well as by adjusting the surface area through which the compositions are administered to skin.

Preferred transdermal drug delivery systems for use herein contain one or more drug/permeation enhancer reservoirs, a backing layer, and optionally one or more additional layers as those skilled in the art of transdermal drug delivery will readily appreciate.

The drug/permeation enhancer reservoir(s) will typically be in the the form of a matrix comprising rubber or other polymeric material, e.g., natural and synthetic rubbers such as polybutylene, polyisobutylene, polybutadiene, polyethylene, styrene-butadiene copolymers, polyisoprene, polyurethane, copolyesters, ethylene/acrylic copolymers, polyether amides, silicones and their copolymers, and butadiene/acrylonitrile copolymers, ethylene vinyl acetate, gelled or thickened mineral oil, petroleum jelly and various agueous gels and hydrophilic polymers that may serve as thickening agents. The matrix is applied to skin using a suitable adhesive as described, for example, in U.S. Pat. No. 4,568,343, supra. In some cases, the matrix may itself be comprised of an adhesive material.

The drug reservoir layer is formulated so as to contain the selected pharmacologically active agent(s) as well as the above enhancer composition. In a preferred embodiment, the layer will contain up to about 15 wt.% drug (e.g., 5 wt.% estrogen, 10 wt.% progestogen, in a preferred contraceptive patch), 5-40 wt.% enhancer composition, e.g., an 80:20 v/v Transcutol/PGML admixture, and up to 4 wt.% silicone oil or mineral oil to serve as a tackifier for the pressure-sensitive adhesive. The pressure sensitive adhesive which serves as the reservoir for this mixture is typically a polyisobutylene, silicone or acrylate adhesive. The layer may be formulated so that the selected drug is contained therein below saturation, at saturation, or in excess.

The backing membrane, which may be either occlusive or nonocclusive, is preferably comprised of a flexible, stretchable, polymer film, e.g., of polyether urethane, polyester urethane, polyamide, or other related copolymers. The material and thickness selected for the backing membrane is preferably such that a transdermal system can be provided having good wearability for at least a seven-day application.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

In vitro Franz flow-through cells were used to compare the penetration of estradiol through skin using different ratios of Transcutol and methyl laurate. A piece of human cadaver skin was mounted between the two half-cells and fastened with a clamp. Two hundred μl of saturated estradiol solutions (prepared with different ratios of Transcutol and methyl laurate, as indicated in Table 1) were applied to the donor compartment to start the experiment. The receiver compartment was filled with 0.1% gentamicin in distilled, deionized water and the temperature was maintained at 32° C. Samples were taken at preset time intervals and assayed by HPLC. The flux was calculated from the slope of the cumulative amounts of estradiol in the receiver compartment vs. time. The results are summarized in Table 1. An increase in skin flux was observed when Transcutol was used in combination with methyl laurate at different ratios. The maximum flux (0.71 μg/cm$^2$/hr) was achieved when the ratio of Transcutol: methyl laurate was 80:20 (v/v) as compared to 0.36 and 0.35 μg/cm$^2$/hr when Transcutol or methyl laurate, respectively, were used alone.

TABLE 1

The effect of binary solutions with Transcutol and methyl laurate on the penetration of estradiol through human cadaver skin

| Vehicle composition | Flux* (μg/cm$^2$/hr) |
| --- | --- |
| Transcutol | 0.35 ± 0.19 |
| Transcutol:methyl laurate (80:20, v/v) | 0.71 ± 0.03 |
| Transcutol:methyl laurate (60:40, v/v) | 0.59 ± 0.12 |
| Transcutol:methyl laurate (40:60, v/v) | 0.47 ± 0.05 |
| Transcutol:methyl laurate (20:80, v/v) | 0.46 ± 0.14 |
| methyl laurate | 0.36 ± 0.16 |

*The experiments were performed in triplicate for each vehicle combination.

EXAMPLE 2

The in vitro Franz flow-through cells were used to compare the penetration of estradiol through skin using different ratios of Transcutol in commercial PGML (obtained from Gattefosse; approximate composition of this "PGML" was determined to be about 50 wt.% propylene glycol monolaurate itself, 40-45 wt.% propylene glycol dilaurate, and 5-10 wt.% propylene glycol). A piece of human cadaver skin was mounted between the two half-cells and fastened with a clamp. Two hundred μl of saturated estradiol solutions (prepared with different ratios of Transcutol and propylene glycol monolaurate, as indicated in Table 2) were applied to the donor compartment to start the experiment. The receiver compartment was filled with 0.1% gentamicin in distilled, deionized water and the temperature was maintained at 32° C. Samples were taken at preset time intervals and assayed by HPLC. The flux was calculated from the slope of the cumulative amounts of estradiol in the receiver compartment vs. time. The results are summarized in Table 2. The skin fluxes increase 2-3 fold when Transcutol was used in combination with propylene glycol monolaurate at different ratios. The flux reached a maximum value of 0.69 μg/cm$^2$/hr, when the ratio of Transcutol to PGML was about 80:20 (v/v). By contrast, fluxes of 0.37 and 0.21 μg/cm$^2$/hr were obtained for propylene glycol monolaurate and Transcutol, respectively, used alone.

TABLE 2

The effect of binary solutions with Transcutol and propylene glycol monolaurate on the penetration of estradiol through human cadaver skin

| Vehicle composition | Flux* (μg/cm$^2$/hr) |
| --- | --- |
| Transcutol | 0.21 ± 0.16 |
| Transcutol:propylene glycol monolaurate (80:20, v/v) | 0.69 ± 0.12 |
| Transcutol:propylene glycol monolaurate (60:40, v/v) | 0.63 ± 0.21 |
| Transcutol:propylene glycol monolaurate (40:60, v/v) | 0.49 ± 0.14 |
| Transcutol:propylene glycol monolaurate (20:80, v/v) | 0.40 ± 0.13 |
| propylene glycol monolaurate | 0.37 ± 0.14 |

*The experiments were performed in triplicate for each vehicle combination.

EXAMPLE 3

The in vitro Franz flow-through cells were used to compare the penetration of norethindrone, norethindrone acetate and levonorgesterol in vehicles having different ratios of Transcutol and methyl laurate. A piece of human cadaver skin was mounted between the two half-cells and fastened with a clamp. Two hundred $\mu l$ of saturated progestogens in solutions (prepared having different ratios of Transcutol and methyl laurate, as indicated in Table 3) were applied to the donor compartment to start the experiment. The receiver compartment was filled with 0.1% gentamycin in distilled, deionized water and the temperature was maintained at 32° C. Samples were taken at preset time interval and assayed by HPLC. The flux was calculated from the slope of the cumulative amounts of progestogens in the receiver compartment vs. time.

The skin fluxes for norethindrone, norethindrone acetate and levonorgesterol from vehicles with different ratios of Transcutol and methyl laurate are summarized in Table 3. The same trend, i.e., an increase in flux when Transcutol was used in combination with methyl laurate, was observed for these three progestogens. The maximum flux was again observed when the ratio of Transcutol to methyl laurate was about 80:20 (v/v). The maximum flux values obtained were 1.55, 1.71 and 0.25 $\mu g/cm^2/hr$ for norethindrone, norethindrone acetate and levonorgesterol, respectively. In comparison, the fluxes for norethindrone, norethindrone acetate and levonorgesterol, with Transcutol alone, were 0.26, 0.63 and 0.09 $\mu g/cm^2/hr$, respectively, and, for methyl laurate alone, were 0.60, 1.03 and 0.12 $\mu g/cm^2/hr$. (It should also be noted that the 60:40 formulations gave slightly lower fluxes than for the 80:20 formulations, but were higher than that of either methyl laurate or Transcutol alone.)

TABLE 3

The effect of binary solutions with Transcutol and methyl laurate on the penetration of norethindrone, norethindrone acetate, and levonorgesterol through human cadaver skin

| Vehicle composition | Flux* ($\mu g/cm^2/h$) | | |
| --- | --- | --- | --- |
| | Norethindrone | Norethindrone acetate | Levonorgesterol |
| Transcutol | 0.26 ± 0.15 | 0.63 ± 0.38 | 0.09 ± 0.03 |
| Transcutol:methyl laurate (80:20, v/v) | 1.55 ± 0.35 | 1.71 ± 0.17 | 0.25 ± 0.05 |
| Transcutol:methyl laurate (60:40, v/v) | 1.01 ± 0.12 | 1.52 ± 0.02 | 0.24 ± 0.02 |
| Transcutol:methyl laurate (40:60, v/v) | 0.80 ± 0.14 | 1.35 ± 0.17 | 0.22 ± 0.03 |
| Transcutol:methyl laurate (20:80, v/v) | 0.65 ± 0.03 | 1.01 ± 0.09 | 0.13 ± 0.02 |
| methyl laurate | 0.60 ± 0.10 | 1.03 ± 0.17 | 0.12 ± 0.02 |

*Experiments were performed in triplate for each vehicle combination.

EXAMPLE 4

The in vitro Franz flow-through cells were used to compare the penetration of norethindrone, norethindrone acetate and levonorgesterol in vehicles containing varying amounts of Transcutol and propylene glycol monolaurate. A piece of human cadaver skin was mounted between the two half-cells and fastened with a clamp. Two hundred $\mu l$ of saturated progestogen solutions (having varying ratios of Transcutol and propylene glycol monolaurate, as indicated in Table 4) were applied to the donor compartment to start the experiment. The receiver compartment was filled with 0.1% gentamicin in distilled, deionized water and the temperature was maintained at 32° C. Samples were taken at preset time interval and assayed by HPLC. The flux was calculated from the slope of the cumulative amounts of progestogens in the receiver compartment vs. time.

The skin fluxes for norethindrone, norethindrone acetate and levonorgesterol from different ratios of Transcutol and PGML are summarized in Table 4. The same trend, i.e., increases in skin flux when Transcutol was used in combination with PGML, was observed for all three progestogens. The maximum flux for norethindrone was 0.79 $\mu g/cm^2/hr$, was observed when Transcutol was combined with propylene glycol monolaurate in an 80:20 (v/v) ratio, as compared to 0.17 and 0.31 for Transcutol and PGML alone, respectively. The maximum fluxes for norethindrone acetate were 1.31 to 1.33 $\mu g/cm^2/hr$ when Transcutol was combined with PGML in 80:20 and 60:40 (v/v) ratios as compared to 0.26 and 0.39 for Transcutol and PGML alone. Similarly, the fluxes for levonorgesterol ranged from 0.06 to 0.09 $\mu g/cm^2/hr$ when Transcutol was used in combination with PGML; the maximum flux was observed at a Transcutol:PGML ratio of 40:60 (v/v). By contrast, the fluxes, for levonorgesterol, were 0.02 and 0.06, respectively, using Transcutol and PGML alone.

TABLE 4

The effect of binary solutions with Transcutol and propylene glycol monolaurate on the penetration of norethindrone, norethindrone acetate and levonorgesterol through human cadaver skin

| Vehicle composition | Flux* ($\mu g/cm^2/h$) | | |
| --- | --- | --- | --- |
| | Norethindrone | Norethindrone acetate | Levonorgesterol |
| Transcutol | 0.17 ± 0.05 | 0.26 ± 0.14 | 0.02 ± 0.01 |
| Transcutol:propylene glycol monolaurate (80:20, v/v) | 0.79 ± 0.19 | 1.31 ± 0.39 | 0.06 ± 0.01 |
| Transcutol:propylene glycol monolaurate (60:40, v/v) | 0.78 ± 0.05 | 1.33 ± 0.03 | 0.07 ± 0.00 |
| Transcutol:propylene glycol monolaurate (40:60, v/v) | 0.77 ± 0.11 | 1.15 ± 0.33 | 0.09 ± 0.01 |
| Transcutol:propylene glycol monolaurate (20:80, v/v) | 0.46 ± 0.03 | 0.49 ± 0.06 | 0.08 ± 0.01 |
| propylene glycol monolaurate | 0.31 ± 0.03 | 0.39 ± 0.04 | 0.06 ± 0.01 |

*Experiments were performed in triplicate for each vehicle combination.

EXAMPLE 5

A series of norethindrone acetate delivery systems was prepared by the following procedures. 2% of the norethindrone acetate (NA) was mixed and sonicated with various ratios of TC and PGML for 10 minutes. Appropriate amounts of the drug-enhancer mixture were then added into a solution of silicone adhesive polymer (Dow Corning silicone #2675) in freon (50 wt.%) and rotated overnight. The drug-enhancer-polymer mixture was then cast on a polyester film (#1022 release liner) with a 8 mil knife. The solvent in the polymer system was evaporated in a 75° C oven for 15 min. The resulting polymer film was laminated with another polyester film (#1022).

Franz flow-through cells were used for in vitro skin flux experiments. The release liners were removed, and the polymer systems made were then laminated on stratum corneum of the human cadaver skin and mounted between the two half-cells and fastened with a clamp. The receiver compartment was filled with 0.1% gentamicin in distilled, deionized water. The temperature was maintained at 32° C. Samples were taken every 8 hours for 3 days and assayed by HPLC. The flux was calculated from the slope of the cumulative amounts of norethindrone acetate in the receiver compartment vs. time. The results of skin flux of norethindrone acetate in these polymer systems were tabulated in Table 5. The flux of norethindrone acetate from polymer systems was increased when Transcutol was used in combination with PGML, relative to Transcutol alone. The norethindrone acetate flux can also be increased by enhancer loading. The flux increased from 0.17 to 0.75 $\mu g/cm^2/hr$ when 20% Transcutol/PGML (80:20, v/v) was incorporated into the polymer system instead of 5%. The flux was increased from 0.29 to 0.45 when 20% of the mixture was incorporated into the polymer instead of 5%.

TABLE 5

Flux of norethindrone acetate from a polymer matrix through human cadaver skin

| Vehicle incorporated | Ratio (NA:Vehicle:Sil.) | Flux* ($\mu g/cm^2hr$) |
|---|---|---|
| TC | 2:10:88 | 0.15 ± 0.01 |
| TC:PGML (80:20) | 2:5:93 | 0.17 ± 0.02 |
| TC:PGML (80:20) | 2:20:78 | 0.75 ± 0.07 |
| TC:PGML (50:50) | 2:10:88 | 0.32 ± 0.05 |
| TC:PGML (20:80) | 2:5:93 | 0.29 ± 0.05 |
| TC:PGML (20:80) | 2:20:78 | 0.45 ± 0.08 |
| PGML | 2:10:88 | 0.42 ± 0.03 |

*Average ± standard deviation; three experiments were performed for each vehicle combination.

EXAMPLE 6

Optimization of the Transcutol/PGML Ratio: This study was designed as a matrix formulation step. It was conducted using Dow Corning silicone polymer #2675 as the matrix contact adhesive in which estradiol and TC/PGML were dispersed, with varying ratios of TC to PGML. The formulations tested are represented in Table 6.

TABLE 6

| TC/PGML Ratio (v/v) | Enhancer (wt. %) | Silicone (wt. %) | Estradiol (wt. %) |
|---|---|---|---|
| 80:20 | | 81 | 5 |
| 60:40 | 14% | 81 | 5 |
| 40:60 | | 81 | 5 |
| 80:20 | | 75 | 5 |
| 60:40 | 20% | 75 | 5 |
| 40:60 | | 75 | 5 |

Methodology: General in vitro skin methodology was as described in the preceding examples.

Skin permeation conditions: temperature, 32° C./; sampling times 7h, 17h, 24h, 48h; n=4. A static vertical Franz cell was used.

Skin preparation: pieces of skin recently excited (aesthetic surgery) prepared according to the method of Kligman.

Assay procedure: estradiol in the receptor compartment was assayed using HPLC at 210 nm using acetonitrile/TEAP buffer, pH 3.

Data analysis: estradiol skin fluxes were calculated by dividing the total amount of E2 permeated by the total duration of the experiment.

Matrices: matrices studied were fabricated with a hand-casting/solvent drying/hand-laminating general process. All matrices were allowed to equilibrate 8-10 days before skin permeation testing was begun.

Results and Discussion: The E2 skin flux values obtained with the different matrices are represented in FIG. 1. The E2 fluxes were in the range of 0.06-0.2 $\mu g/cm^2/hr$ for the different matrices tested. In a general way, the 20% loading gave higher fluxes than the 14% loading. For the two E2 loadings, 14% an d20%, there was a significant increase in E2 flux as the TC/PGML ratio decreased. With 14% loading, the highest flux was obtained with a TC/PGML ratio of 40:60, while with 20% loading, the highest flux was obtained with a TC/PGML ratio of 60:40.

This study permits one to conclude that the TC/PGML ratio should be optimized when the drug-/enhancer composition is dispersed in a polymer medium.

We claim:

1. A transdermal delivery system for administering at least one pharmacologically active agent to a patient, comprising:
   (a) a source of the at least one pharmacologically active agent to be administered;
   (b) a source of a permeation enhancer composition comprising an ether component selected from the group consisting of diethylene glycol monoethyl ether, diethylene glycol monomethyl ether, and mixtures thereof, and an ester component given by the formula $[CH_3(CH_2)_mCOO]_nR$, in which m is an integer in the range of 8 to 16, n is 1 or 2, and R is a lower alkyl ($C_1$–$C_3$) residue that is either unsubstituted or substituted with one or two hydroxyl groups, wherein the ratio of ether to ester in the enhancer composition is in the range of about 90:10 to 40:60 (v/v); and
   (c) a means for maintaining the transdermal delivery system in agent and enhancer composition transmitting relationship to the skin.

2. The system of claim 1, wherein n is 10.

3. The system of claim 1, wherein the ether component is diethylene glycol monoethyl ether.

4. The system of claim 1, wherein the ether component is diethylene glycol monoethyl ether and the ester component is propylene glycol monolaurate or propylene glycol monolaurate in combination with propylene glycol dilaurate.

5. The system of claim 1, wherein the ester component is a lower alkyl ($C_1$–$C_3$) laurate.

6. The system of claim 2, wherein the at least one pharmacologically active agent is a steroid.

7. The composition of claim 4, wherein the at least one pharmacologically active agent comprises a progestogen, an estrogen, or a mixture thereof.

8. The composition of claim 4, wherein the progestogen is norethindrone or norethindrone acetate, and the estrogen is estradiol.

9. A transdermal delivery system for administering at least one pharmacologically active agent to a patient, comprising:
   a drug reservoir comprising a polymeric adhesive matrix;
   a backing layer laminated thereto, comprising a flexible polymer film; and
   contained with the reservoir, a selected pharmacologically active agent, and an enhancer composition comprising an ether component selected from the group consisting of diethylene glycol monoethyl ether, diethylene glycol monomethyl ether, and mixtures thereof, and an ester component given by the formula $[CH_3(CH_2)_mCOO]_nR$, in which m is an integer in the range of 8 to 16, n is 1 or 2, and R is a lower alkyl ($C_1$–$C_3$) residue that is ether unsubstituted or substituted with one or two hydroxyl groups, wherein the ratio of ether to ester in the enhancer composition is in the range of about 90:10 to 40:60 (v/v).

* * * * *